United States Patent
Hertz

(10) Patent No.: US 10,779,912 B2
(45) Date of Patent: Sep. 22, 2020

(54) DENTAL IMPLANT SYSTEM

(71) Applicant: Paul Hertz, Riverdale, NY (US)

(72) Inventor: Paul Hertz, Riverdale, NY (US)

( * ) Notice: Subject to any disclaimer, the term of this patent is extended or adjusted under 35 U.S.C. 154(b) by 0 days.

(21) Appl. No.: 14/886,087

(22) Filed: Dec. 19, 2015

(65) Prior Publication Data

US 2017/0172710 A1 Jun. 22, 2017

(51) Int. Cl.
*A61C 8/00* (2006.01)
*A61B 6/14* (2006.01)
*A61B 6/03* (2006.01)
*A61C 9/00* (2006.01)
*A61C 13/00* (2006.01)

(52) U.S. Cl.
CPC ............ *A61C 8/0009* (2013.01); *A61B 6/032* (2013.01); *A61B 6/14* (2013.01); *A61C 9/0053* (2013.01); *A61C 13/0004* (2013.01)

(58) Field of Classification Search
CPC . A61C 8/0009; A61C 9/0053; A61C 13/0004; A61C 19/04; A61C 19/043; A61C 19/045; A61C 1/082; A61C 19/055; A61C 13/008; A61C 13/0089; A61B 6/032; A61B 6/14
USPC ........... 433/72, 75, 76, 102, 172–175, 201.1
See application file for complete search history.

(56) References Cited

U.S. PATENT DOCUMENTS

| | | | | |
|---|---|---|---|---|
| 3,386,169 A | * | 6/1968 | Scialom | A61C 8/0028 433/173 |
| 3,449,830 A | * | 6/1969 | Bernard | A61C 13/26 433/215 |
| 3,790,507 A | * | 2/1974 | Hodosh | A61C 8/0012 260/998.11 |
| 5,725,376 A | * | 3/1998 | Poirier | A61C 1/084 433/172 |
| 5,897,696 A | * | 4/1999 | Giordano | A61L 31/08 106/181.1 |
| 2005/0282106 A1 | * | 12/2005 | Sussman | A61C 1/084 433/76 |
| 2007/0111156 A1 | * | 5/2007 | Gittelson | A61C 1/084 433/72 |
| 2008/0085489 A1 | * | 4/2008 | Schmitt | A61C 1/084 433/75 |
| 2010/0003634 A1 | * | 1/2010 | Cousley | A61C 8/00 433/72 |
| 2015/0190209 A1 | * | 7/2015 | Suttin | A61C 1/084 433/76 |
| 2016/0074141 A1 | * | 3/2016 | Lozada | A61C 8/0089 433/75 |

* cited by examiner

*Primary Examiner* — Sean M Michalski
*Assistant Examiner* — Mirayda A Aponte
(74) *Attorney, Agent, or Firm* — Budzyn IP Law, LLC

(57) ABSTRACT

A dental implant and final prosthetic placement system for small-diameter implants (and method for using the system) in which a final prosthetic is digitally designed and created, and is itself used as the drill guide to place the implants. The final prosthetic is held in the predetermined proper drilling position by a stent, such as an occlusal guard. The combination of final prosthetic (with holes through which the small-diameter implants are drilled to secure it) and the stent encasing the final prosthetic, is itself the drill guide.

2 Claims, 3 Drawing Sheets

DENTAL IMPLANT SYSTEM

CROSS-REFERENCES

This patent application depends for priority on Provisional Application 62/094,617 filed on Dec. 19, 2014. This application is incorporated herein by reference, but is not admitted to be prior art with respect to the present invention by its mention in the background.

BACKGROUND

Traditional implant dentistry is typically a time-consuming and expensive process with multiple steps required over many weeks or months to scan the edentulous area for available bone, drill and place the implant, and allow for osseointegration and healing. Placement of the implant is particularly difficult for dental surgery professionals, as the location of available bone for drilling is often complicated to discern with traditional methods.

The key to success of cases using embodiments of the present implant system is maintaining the final prosthetic appliance in the proper position for placement. This is accomplished by a novel system in which the implant creation and placement is performed in reverse order. The prosthetic is created before any of the implants are placed. The prosthetic tells any dental surgeon exactly where to drill, so he is able to do so based solely on the final prosthetic appliance, bypassing the time-consuming and expensive steps necessary in traditional dental implant surgery. The patient can—in a matter of minutes—walk out of the dentist's office with teeth.

For the foregoing reasons, there is a need for a system that can inexpensively and quickly create a drill guide to be used in dental implant surgery without the complications associated with traditional implant dentistry.

SUMMARY

The present invention is directed generally to a dental implant system and methods, and specifically to mini implant methods that reduce the need for the complications associated with traditional implant dentistry.

The model of the patient's mouth ("stone") and the model of the drill guide are created using intraoral digital scanning. The word "stone" should not be restricted to any specific material, as the solid model could be made of many other materials. A computed tomography (CT) scan of the patient's edentulous and surrounding area are also obtained. These images are linked. Such oral CT scans—the digital scans as well as the linking—are well-known in the art to find available bone for implant placement. Once the CT scan has been performed, it is possible, and well-known in the art, to construct a surgical implant drill guide that would allow the dental surgeon to predetermine implant locations virtually, and surgically place them using computer added designing (CAD)/computer added machining (CAM) technology. In the first step of the dental implant system described herein, we are using traditional methods to virtually place the implants and then create the final prosthetic based upon the linked data from the CT scan, and the intraoral digital scan based on traditional CAD/CAM technology.

Two of the virtual implants have been created parallel and virtual analogues are added to the design of the edentulous space to be restored. The virtual analogues will go through the final prosthesis and extend beyond the device. This is then turned into a solid model (via 3d printing, for example) of the edentulous ridge with projecting parallel implant analogues.

The final prosthetic is then placed and secured by the analogues and the model of the ridge. Onto this unit, a stent is created, encasing the prosthesis, which fits firmly to the edentulous area of the stone. The drill guide is the stent/prosthesis combination. It sits directly on the mouth, on the precise spot on the arch where drilling is to occur. From here, everything is in place for the patient to receive a dental implant without the expense of time, energy, and money that traditional methods require. Only local anesthetic infiltration is necessary. Because the scan is created using a CT scan and CAD/CAM technology, the drill guide sits directly on the edentulous area. In some embodiments, the CAD/CAM methods of creating the analog and stone are accomplished by 3D printing.

An occlusal guard ("stent") may encase and support the final prosthesis, assuring that it cannot move freely. It is necessary for the stent not to move freely, because it serves to secure the final prosthetic in place on the edentulous area of the mouth. The stent, with incorporated final prosthesis, can be secured with a stainless steel or the like security pin placed through the lateral stent into holes pre-established into safe available bone. Usually surrounding teeth will be adequate support, and the pins will not be necessary. Access to the screw guide holes in the final restoration may be maintained through the stent. In some embodiments, metal protective shields cross the stent over the final prosthesis on key locations to eventually act as separation guides. After implant placement, these protective shields show the dentist where to safely cut the stent in order to release the final prosthesis from the stent. If support pins had been used, they are now removed, and the pieces of the stent are removed and discarded, leaving the final prosthesis in place as a permanent restoration.

In this patent, the "final prosthetic" is both the drill guide and the implant placement guide. It has positive apical stops for the implants which eliminate the need for guide and reference pins. The holding "stent" is removed post implant placement leaving the "final prosthetic"/"drill guide" unit in the patients mouth on the date of implant placement. Only the "stent" which holds the prosthetic is removed. Unlike in the prior art, it is desirable in this concept to place multiple divergent small-diameter implants to support the "final prosthesis."

These and other features, aspects, and advantages of the present invention will become better understood with regard to the following description, appended claims, and accompanying drawings. It is to be understood that the foregoing summary addresses only a few exemplary aspects of the invention, and that both the foregoing general description and the following detailed description are exemplary and explanatory only and are not restrictive of the invention as claimed.

DESCRIPTION

Figure 1:
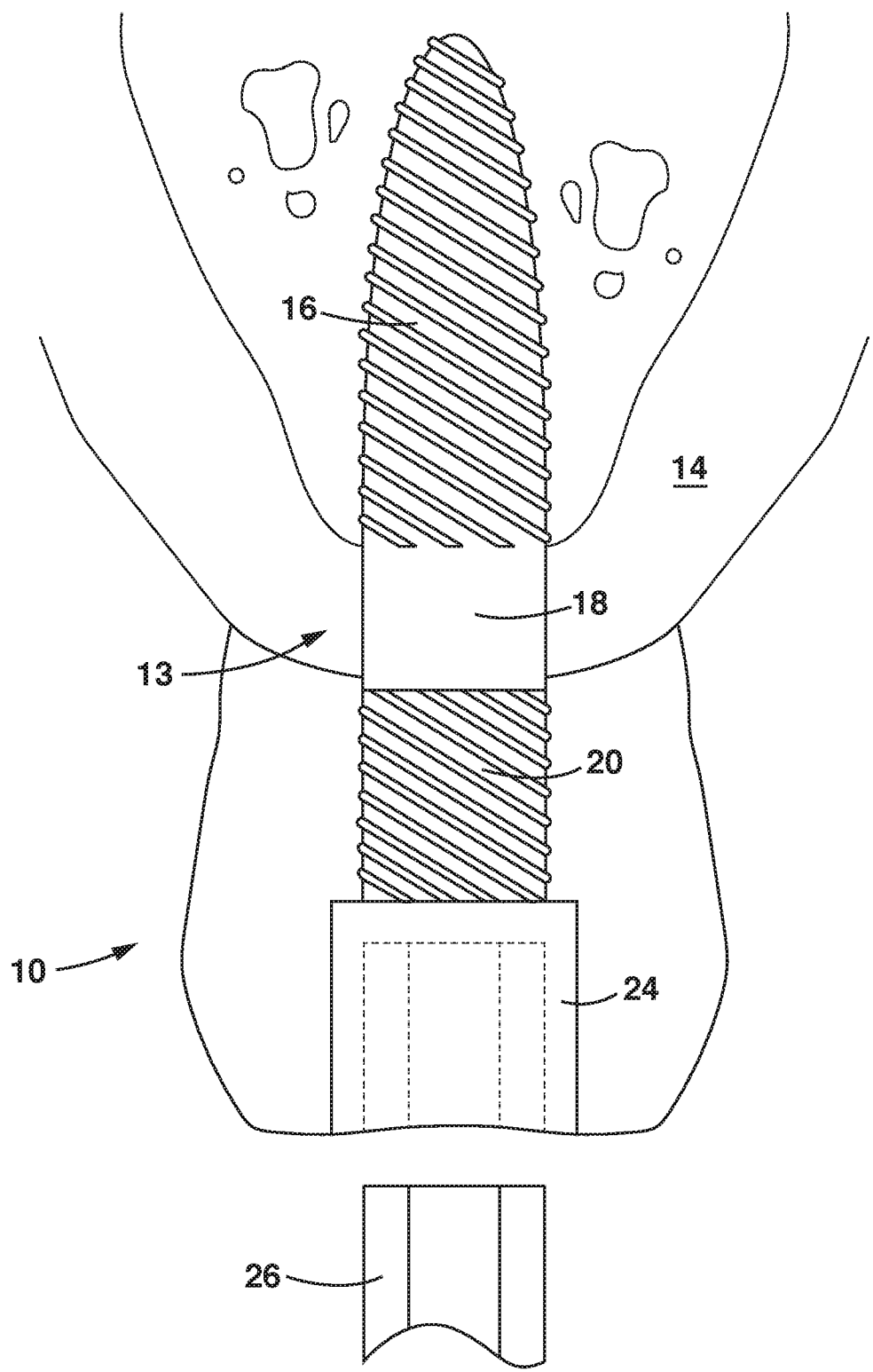
FIG. 1 is a view of the implant being drilled into the gingiva and engaging the acrylic stent.

FIG. 1 is a schematic illustration of a dental implant system in accordance with an embodiment of the present invention. The system involves both a final restoration drill guide 12 and a method for creating and using the drill guide. The method comprises taking a CT scan of the patient's edentulous and surrounding area; developing a laboratory model of the arch with missing teeth to be replaced in stone or some other solid material, the analog, the final prosthetic 10 and the stent 11; creating physical models of the stone, the analog, the final prosthetic 10 and the stent 11; placing the stent 11 in position on the patient; and drilling the final prosthesis 10 into the gingiva 14 with small-diameter implants. Small-diameter implants are understood in the art to mean implants with a diameter less than 3.2 mm. In some embodiments, the method further comprises cutting off the stent 11 after drilling in order to release the final prosthesis 10 in final position.

Taking a CT scan of a patient's edentulous and surrounding area is well-known in the dental arts, as is the ability to develop first a laboratory model, and then a physical model of the arch, analog, and stent 11, using CAD/CAM technology. A major innovation of the present invention is the single article of manufacture which comprises a stent 11 made on the model, already supporting the final prosthesis 10. The stent 11 encases the final prosthesis 10, assuring that it cannot move freely.

Figure 2:
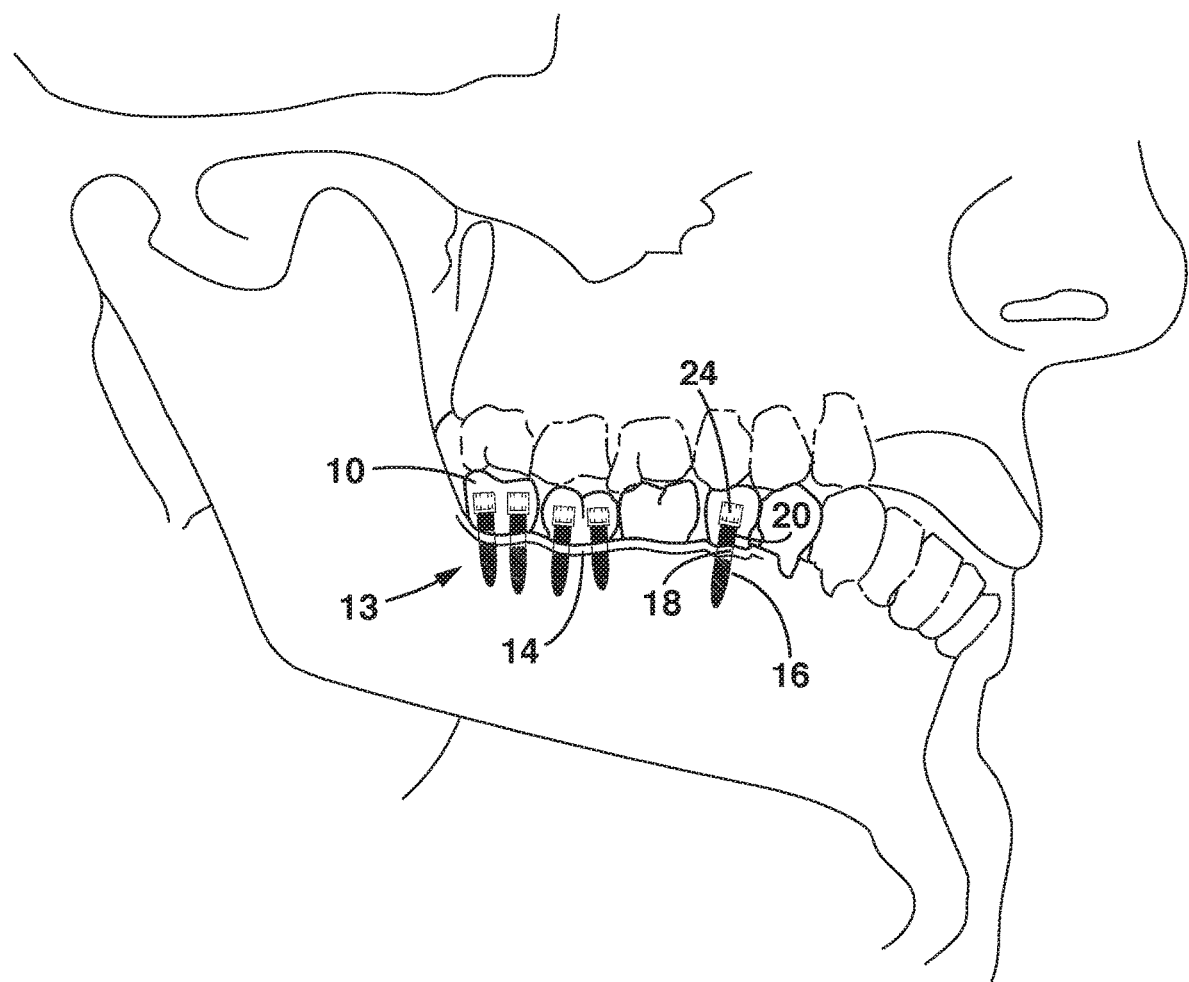
FIG. 2 is a side view of the final prosthesis and stent in place.
Figure 3:
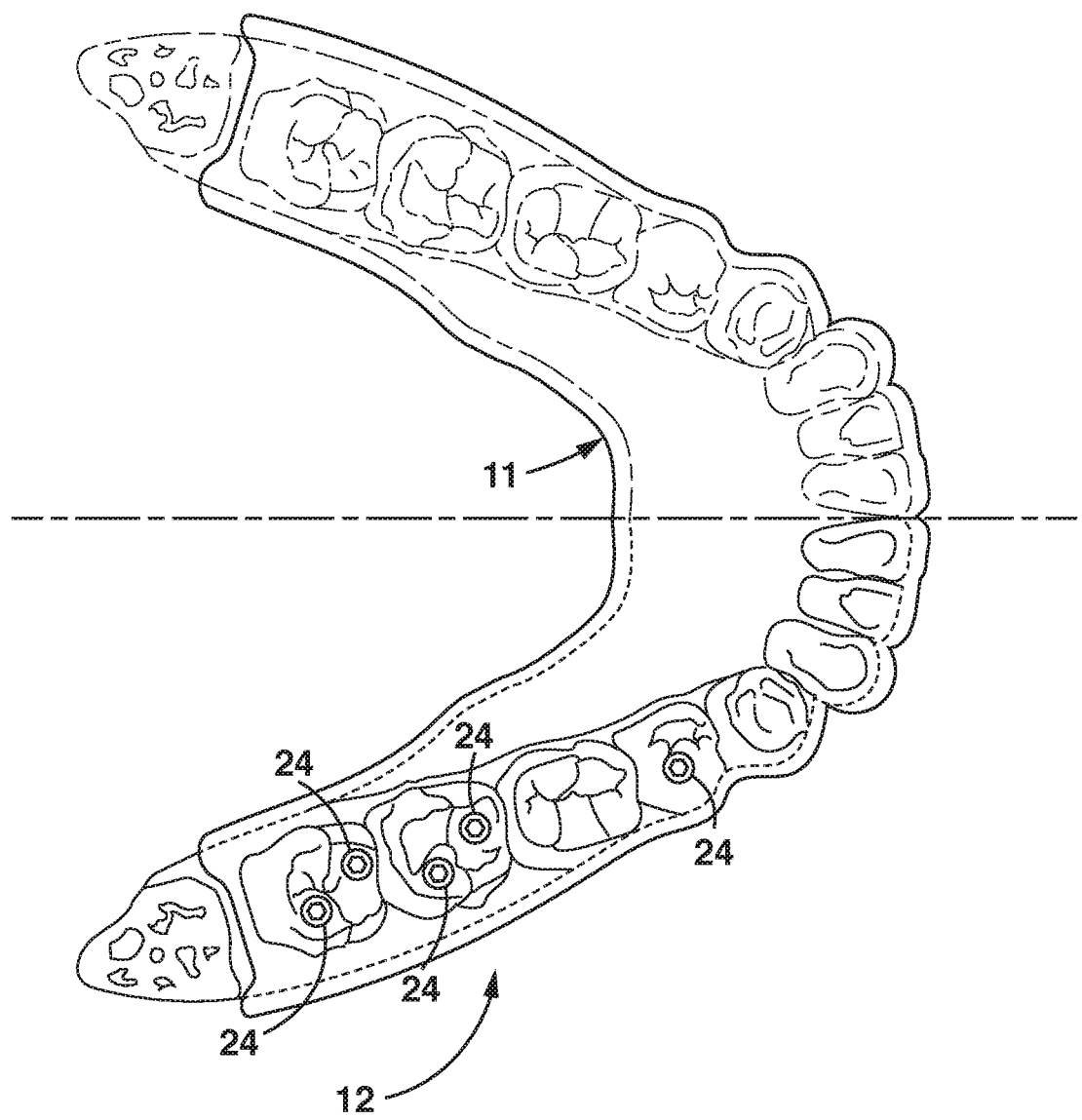
FIG. 3 is a top view of the final prosthesis and stent in place.

FIG. 2 is a side view of the final prosthesis 10 and stent 11 held securely in place. Together, this comprises the drill guide 12.

Once the drill guide 12 is in final position on the patient, in some embodiments, single small-diameter implants 13 will be used to replace anterior and pre-molar teeth of about 3 mm diameter. In some embodiments, two about 2=implants 13 (collectively, "small-diameter implants") will be used for each molar replacement (preferably distal and mesiolingual).

The active (cutting) section 16 of the small-diameter implants 13 can be, for example, from 6 mm to 16 mm in length. Above this is the 3 mm gingival collar 18. Above this segment is the between 3 mm and 7 mm segment 20 with deeper threads that engage the final prosthesis. In some embodiments, the 5 mm segment 20 will have no threads, but will be smooth. Finally is the implant head 24 which is also 5 mm in height and may, for example, have a hollowed 4 mm deep internal hex pattern to accept the torque driver 26.

In some embodiments, the tip of the active section 16 of the implants 13 will be covered with a 5 mm nylon sleeve, which does not touch the conical point of the tip as it narrows. This sleeve will be used as a drill guide for the implant 13, ensuring that it is introduced into the prosthesis with the proper inclination. The implant 13 will act as a screw to hold the prosthetic, and the stent 11 encases or is otherwise connected to the prosthetic. The sleeve then stays in place as the implant 13 advances into bone. After drilling, the sleeve acts as a stop for the head of the implant 13. The sleeve advances with the implant until it rests on a ledge/platform which halts its forward movement as the implant 13 proceeds into the bone, and then stops progression of the implant 13 when the implant head 24 rests on the sleeve's superior segment.

This equates to single piece implants measuring, for example, between 21 mm and 29 mm. All measurements in the preceding paragraphs are by way of example only, and are not restrictive of the invention as claimed.

In the invention described herein, two of the implants 13 can be parallel, and the others divergent, in order to prevent the stent 11 or final prosthetic 10 from moving freely, securing the implants in place. The prosthetic 10 is kept in place by the stent 11 as the implant 13 advances into the bone.

In the foregoing description, various features are grouped together in a single embodiment for purposes of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this description, with each claim standing on its own as a separate embodiment of the invention.

Although the present invention has been described in considerable detail with reference to certain preferred versions thereof, other versions are possible. Therefore, the spirit and scope of the appended claims should not be limited to the description of the preferred versions contained therein.

The invention claimed is:

1. A dental implant system, comprising:
   a first final prosthesis which contains two or more holes;
   a stent encasing the first final prosthesis, the stent being configured to hold the first final prosthesis in the proper drilling position; and,
   a plurality of small-diameter implants placeable through the two or more holes of the first final prosthesis, each of the small-diameter implants having a coronal end and an apical end, wherein, an implant head is provided at the coronal end with an at least partially threaded shank extending apically from the implant head to the apical end, an annular apically-facing shoulder is defined by the implant head radiating outwardly from the at least partially threaded shank,
   wherein the stent is configured to extend across a patient's dental arch to hold the first final prosthesis in the proper drilling position so that the plurality of small-diameter implants are drilled, with the apical ends leading, into the patient's gingiva and bone through the two or more holes to implant the small-diameter implants in the patient's gingiva and bone, wherein, the small-diameter implants are implanted (i) so that the implant heads of the small-diameter implants are spaced apart, (ii) so that the implant heads do not protrude from the first final prosthesis, (iii) so as to have longitudinal axes diverging away from one another in the direction of the apical ends, and (iv) so that the shoulders of the implant heads are in pressing contact with, recessed within, the first final prosthesis, thereby ensuring that the first final prosthesis is secured and cannot move freely relative to the patient's gingiva and bone.

2. A method of using a dental implant system to place dental implants, comprising;
   taking, using imaging equipment, a CT scan and intraoral digital scan of a patient's edentulous and surrounding area;
   using said CT and intraoral digital scans to determine the number and location of implants;
   using said CT and intraoral digital scans to create a first final prosthesis;
   encasing said first final prosthesis in a stent;
   providing a plurality of small-diameter implants, each of the small-diameter implants having a coronal end and an apical end, wherein, an implant head is provided at the coronal end with an at least partially threaded shank extending apically from the implant head to the apical end, an annular apically-facing shoulder is defined by the implant head radiating outwardly from the at least partially threaded shank;

with the stent extending across a patient's dental arch and holding the first final prosthesis in the proper drilling position, drilling the small-diameter implants, with the apical ends thereof leading, through said first final prosthesis into the patient's gingiva (i) such that the implant heads of the small-diameter implants are spaced apart, (ii) such that the implant heads do not protrude from the first final prosthesis, (iii) such that the longitudinal axes of the small-diameter implants diverge from one another in the direction of the apical ends, and (iv) such that the shoulders of the implant heads come into pressing contact with, recessed within, the first final prosthesis;

removing the stent, leaving the first final prosthesis in position secured to the patient's gingiva.

\* \* \* \* \*